(12) United States Patent
Loussouarn et al.

(10) Patent No.: US 6,993,168 B2
(45) Date of Patent: Jan. 31, 2006

(54) SYSTEM AND PROCESS FOR THE ANALYSIS AND PREDICTIVE SIMULATION OF THE TEMPORAL EVOLUTION OF A HAIR REGION, AND MORE PARTICULARLY OF THE HUMAN SCALP

(75) Inventors: Geneviève Loussouarn, Clichy (FR); Bruno Bernard, Neuilly-sur-Seine (FR); Albert Goldbeter, Brussels (BE); José Halloy, Brussels (BE)

(73) Assignee: L'Oreal, Paris (FR)

( * ) Notice: Subject to any disclaimer, the term of this patent is extended or adjusted under 35 U.S.C. 154(b) by 605 days.

(21) Appl. No.: 09/731,969

(22) Filed: Dec. 8, 2000

(65) Prior Publication Data

US 2001/0006555 A1 Jul. 5, 2001

(30) Foreign Application Priority Data

Dec. 21, 1999 (FR) .................................. 99 16170

(51) Int. Cl.
*G06K 9/00* (2006.01)
(52) U.S. Cl. ...................................... 382/128; 128/922
(58) Field of Classification Search ................ 382/128; 128/922; 250/461.2; 356/39, 40, 41, 42; 377/10, 11, 12
See application file for complete search history.

(56) References Cited

U.S. PATENT DOCUMENTS

| | | | | |
|---|---|---|---|---|
| 5,060,171 A | | 10/1991 | Steir et al. | |
| 5,331,472 A | * | 7/1994 | Rassman | 359/894 |
| 5,764,233 A | | 6/1998 | Brinsmead et al. | |
| 5,777,619 A | * | 7/1998 | Brinsmead | 345/419 |
| 6,162,212 A | * | 12/2000 | Kreindel et al. | 606/9 |
| 6,389,150 B1 | * | 5/2002 | Amornsiripanitch | 382/100 |
| 6,581,011 B1 | * | 6/2003 | Johnson et al. | 702/19 |
| 6,651,008 B1 | * | 11/2003 | Vaisberg et al. | 702/21 |
| 2001/0017936 A1 | | 8/2001 | Loussouarn | |

FOREIGN PATENT DOCUMENTS

| | | |
|---|---|---|
| EP | 0 092 075 | 10/1983 |
| EP | 0 725 364 A2 | 8/1996 |

OTHER PUBLICATIONS

Courtois et al. (M.Courtois, G. Loussouran, S. Hourseau, and J.F. Grollier; British Journal of Dermatology; "Periodicity in the growth and shedding of hair," vol. 134; pp. 47-54).*

(Continued)

*Primary Examiner*—Samir Ahmed
*Assistant Examiner*—Anand Bhatnagar
(74) *Attorney, Agent, or Firm*—Nixon & Vanderhye P.C.

(57) ABSTRACT

System for the simulation of the evolution of a region of the scalp of a subject over time, comprising a means of observation of the said hair region able to output digital observation data, a first digital data processing means capable of classifying elementary parts of the said region on the basis of the observation data, a second digital data processing means capable of simulating the evolution of the said hair region as a function of the data emanating from the first digital data processing means, and a means of displaying the data emanating from the second digital data processing means.

31 Claims, 3 Drawing Sheets

OTHER PUBLICATIONS

Liposcak et al, "Face Recognition from Profiles Using Morphological Operations", Proceedings International Workshop on Recognition, Analysis, and Tracking of Faces and Gestures in . . . ICCV'99 (CAT No. PR00378), Corfu, Greece Sep. 26-27, 1999, pp. 47-52, XP002152958, 1999, Los Alamitos, CA, USA, IEEE Comput. Soc, USA, ISBN: 0-7695-0378-0.

Daldegan et al, "Creating Virtual Fur and Hair Styles for Synthetic Actors", Communicating with Virtual Worlds, Proceedings of Computer Graphics International '93, Lausanne, Switzerland, Jun. 21-25, 1993, pp. 358-370, XP000961750, 1993, Tokyo, Japan, Springer-Verlag, Japan, ISBN: 4-431-70125-7.

* cited by examiner

SYSTEM AND PROCESS FOR THE ANALYSIS AND PREDICTIVE SIMULATION OF THE TEMPORAL EVOLUTION OF A HAIR REGION, AND MORE PARTICULARLY OF THE HUMAN SCALP

The present invention relates to the field of cosmetics and more particularly to the evolution of the human head of hair over the course of a lifetime.

The phenomenon of hair growth and loss in the human species, more particularly in the male sex, is complex and differs from animal species through at least two criteria:

there are very few animal species which, with age, progressively lose their fur;

animal species may experience seasonal moulting on account of the fact that the cycles of the strands are synchronized, that is to say all the strands grow or are lost at the same time.

In man, the hairs are generated by the hair follicles implanted in the scalp. A healthy head of hair is said to contain between 100 000 and 150 000 hairs, and each hair within this head of hair possesses its own cycle.

This life cycle is broken down into three generally successive physiological phases:

a phase of hair growth, referred to as Anagen (A), which may last from a few weeks to 10 years, a transient phase of involution of the follicle and ceasing of hair growth with degeneration of the root, known as Catagen, of the order of a few weeks, a phase of shedding of the hair with the root moving up towards the surface, known as Telogen (T), lasting 1 to 5 months.

At the end of this last phase, the hair therefore disappears from the scalp and this Disappearance (D) may extend from a few days to a few months before the follicle is reactivated to give a new hair in the anagen growth phase.

After a certain number of cycles, the follicle permanently ceases its production and the hair may be regarded as Dead (Dd).

Figure 2:
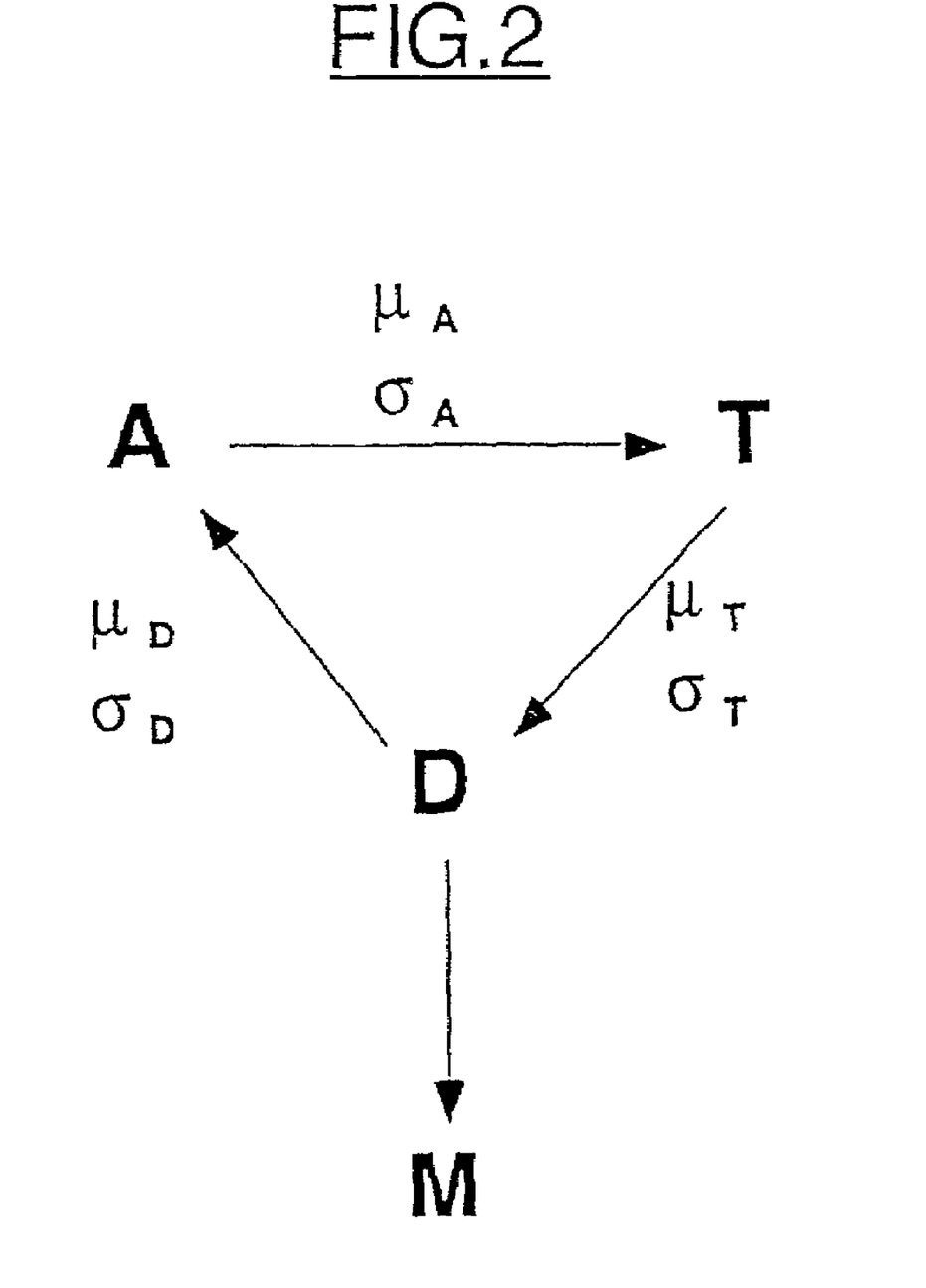
FIG. 2 is a diagrammatic view showing the evolution of the hairs between the various phases.

Given the ratio of the durations of the various phases of the life cycle of the hair, in practice, the Catagen phase which is the shortest is rarely observed; this is why the person skilled in the art prefers to reckon the Anagen (A), Telogen (T) and Disappearance (D) phases. FIG. 2 shows how these phases are strung together in the course of the hair's cycle.

The phenomenon of ageing, over the course of a lifetime, leads over about ten years to a shortening of the growth phases (A) and consequently to an increase in the proportion of the hairs in the loss phase (T). This phenomenon may be accelerated in the case of alopecia which more particularly afflicts men but also women, and which in its final stage leads to baldness, or total shedding of the head of hair.

Since the phases of the hair cycle unravel over long durations, especially the growth phase (A), it follows that the observation of the state of the hairs of a region of the scalp at a precise instant constitutes merely an instantaneous measurement which cannot forecast the future evolution.

Specifically, the current state of the art does not make it possible by observing and quantifying the state of the hair of a young 25-year-old person to forecast and/or illustrate what the state of his head of hair will be when he reaches 60 years of age.

The aim of the present invention is to simulate the chronological evolution of a head of hair on the basis of the smallest possible number of measurements.

The system, according to the invention, is intended for the simulation and for the predictive analysis of the evolution of a region of the scalp of a subject over time, and whose extension to the entire scalp makes it possible to illustrate the overall evolution of the head of hair.

The system comprises a means of observation of the said hair region able to output digital observation data, a first digital data processing means capable of classifying elementary parts of the said region on the basis of the observation data, a second digital data processing means capable of simulating the evolution of the said hair region as a function of the data emanating from the first digital data processing means, and a means of displaying the data emanating from the second digital data processing means, the data output by the first processing means comprising at least one classification according to the duration of the phases of the hair cycle.

Advantageously, the observation data, output by the first processing means, comprise the surface density of hairs, the proportion A (as a %) of hairs in the anagen phase, the proportion T of hairs in the telogen phase (as a %), the proportion D of disappeared hairs (as a %), the proportion Dd of dead hairs (as a %) and the individual rate of growth of the hairs.

Advantageously, the second processing means comprises a means for applying to each observed hair a duration of continuation in its prevailing phase, on the basis of a statistical distribution of the phase durations and of a random number. The distribution is of the log-normal or negative-exponential type or else bell-shaped with the form illustrated in FIG. 3.

In one embodiment of the invention, the second processing means comprises a means for estimating the number of cycles $n_c$ performed by an observed hair, and for comparing it with a predetermined maximum number of cycles $N_k$, a cycle being defined by the successive passage through the three states, anagen, telogen and disappeared.

In one embodiment of the invention, the second processing means comprises a matrix of probabilities of transition from one phase to another phase.

In another embodiment of the invention, the second processing means comprises a means for allocating a given duration of phase to a hair.

The means for allocating a given duration of phase to a hair comprises a random number generator and a means for comparing the said random number with aggregate probabilities of phase transition.

In one embodiment of the invention, the second processing means comprises a matrix representative of the influence of data relating to neighbouring hairs on the transition from one phase to another phase.

In one embodiment of the invention, the second processing means comprises a table representative of the evolution of the mean values of duration of the anagen, telogen and disappearance phases.

In one embodiment of the invention, the system comprises a means for performing a third processing for simulating the evolution of the entire head of hair of the subject on the basis of the data emanating from the second processing.

In one embodiment of the invention, the system comprises a means for associating data from simulating the head of hair which may possibly be associated with other data relating to the evolution of other sites, for example, the face, especially the evolution of the number of wrinkles, the modifications from ageing of the face, any clinical sign associated with ageing with the data emanating from the third processing means.

The subject of the invention is also a process for the simulation and predictive analysis of the evolution of a region of the scalp of a subject over time, in which:

the said hair region is observed so as to provide observation data. The said observation may comprise any appropriate means for collecting photographic and videographic, analogue or digital images or any other means of imaging obtained through a physiology-friendly non-invasive route, including those requiring no particular preparation of the scalp, a first digital processing of the observation data is performed so as to classify elementary parts of the said region, a second digital processing is performed so as to perform a simulation of the temporal evolution of the said hair region as a function of the data emanating from the first digital processing means, and data emanating from the second digital processing are displayed.

Advantageously, at least two observations are performed separated by a first given duration, each observation being preceded by a step of shaving the said hair region, the shaving step being separated from the corresponding observation by a second given duration, in such a way that an evolution of the said hair region can be noted.

The first given duration may lie between one and ten weeks, preferably between two and six weeks, for example of the order of one month. The second given duration may lie between one and ten days, preferably less than five days, for example of the order of two days.

The said hair region may undergo, during a first observation, a marking remaining visible at least up to a second observation.

In one embodiment of the invention, the observation data comprise the surface density of hairs, the proportion A of hairs in the anagen phase, the proportion T of hairs in the telogen phase, and the individual rate of growth of the hairs.

Preferably, the second digital processing takes into account the ratios of the durations of the anagen and telogen phases.

Advantageously, a third digital processing is performed so as to perform a simulation of the temporal evolution of the entire head of hair of the subject on the basis of the data emanating from the second digital processing and the data emanating from the third digital processing are displayed.

The displaying of the said data emanating from the third digital processing can be performed by flat projection, for example as a projection of the type used in cartography, especially a conical Lambert projection.

Data from simulating the evolution of the face (method known as morphing) may possibly be associated with the data emanating from the third digital processing and the associated data may possibly be displayed.

In one embodiment of the invention, it is also possible to simulate the evolution of a region of the scalp which has undergone a modification of aesthetic type.

The observation data may emanate from a phototrichogram, videotrichogram or any other non-invasive method making it possible to assess the state of the cycles of the observed hairs.

Stated otherwise, the simulation system associates the establishing of initial observation data, on the basis of a region of small area, regarding the number of hairs, the proportions of the latter in each phase, the duration of their respective cycles, the mathematical modelling of the latter which makes it possible to extend the evolution of each parameter to the short, medium or very long term, and the application of this modelling to the extension of the entire head of hair for display by an imaging means.

The state of the head of hair can be simulated over various durations lying between 3 months and 100 years, with the aim of predicting its natural evolution or its evolution modified by external or internal causes.

The present invention will be better understood on studying the detailed description of a few embodiments taken by way of wholly non-limiting examples and illustrated by the appended drawings in which.

Figure 1:
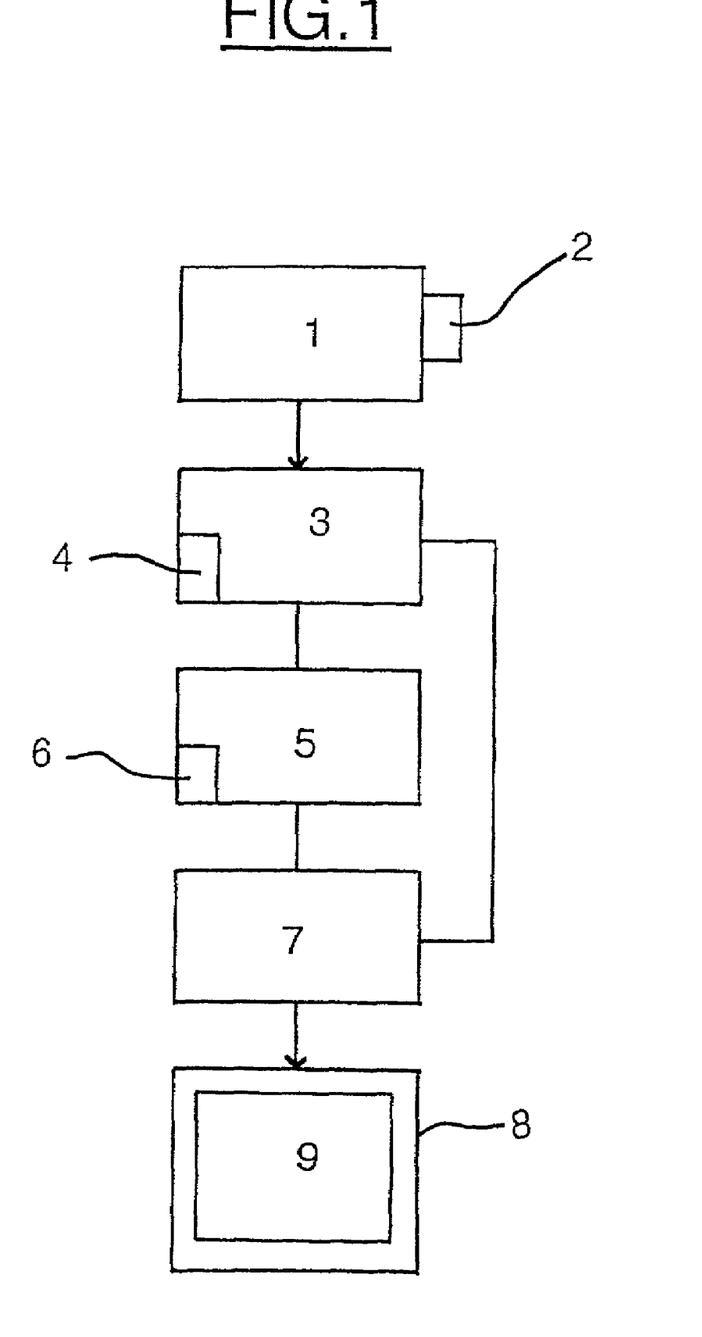
FIG. 1 is a diagrammatic view of the simulation system in accordance with the invention.

As may be seen in FIG. 1, the simulation system in accordance with the invention comprises a camera 1, for example of CCD type, equipped with an objective 2, intended for observing a specified hair region, for example a region of 1 $cm^2$ or the entire head of hair.

The system also comprises a classification means 3 receiving the digital data emanating from the camera 1.

The classification means 3 is provided with a memory 4 allowing among other things the storage of the said data originating from the camera 1.

The classification means 3 is capable of determining the anagen, telogen or disappeared state, in which the hair can be catalogued in an elementary part of the observed region of the scalp.

Stated otherwise, the classification means 3 receives as input an image file representative of the hair region observed and in which each elementary zone is assigned a grey level or colour characteristics, and outputs a file in which each elementary zone is assigned a state, anagen, telogen or disappeared, and possibly other characteristics.

It should be noted that an elementary zone output by the classification means 3 may group together several pixels of the image captured by the camera 1.

The simulation system comprises a simulation means 5 provided with a memory 6 and linked to the classification means 3 so as to receive the classified data comprising in particular the two-dimensional coordinates of a hair follicle, the prevailing phase of the corresponding hair together with the rate of growth of the said hair.

The classification means 3 can also transmit to the simulation means 5, data relating to the surface density of hair, to the proportion A of hairs in the anagen phase, to the proportion T of hairs in the telogen phase, to the proportion D of disappeared hairs, and to the proportion Dd of dead hairs.

The simulation means 5 is capable of outputting data for forecasting the individual state of each hair at a future instant.

Stated otherwise, the simulation means 5 provides a file containing the coordinates of a hair follicle, the phase which the corresponding hair will be in at a future date, and the date for which the simulation was carried out.

The system furthermore comprises a means 7 for generalizing the simulation to the entire head of hair of a user.

On the basis of the simulation data originating from the simulation means 5, of which the data generally relate to only a small area, for example of the order of 1 $cm^2$, the generalization means 7 is able to output data similar to those provided by the simulation means 5 but covering a larger expanse desired by the user, for example the entire scalp.

The generalization means 7 also receives data originating from the classification means 3 insofar as the camera 1 will, with the aim of generalization, capture at least one general image of the area in respect of which one wishes to perform the generalization, in particular the scalp, so as to be able to extend the results of the simulation to this larger area.

A display means 8 such as a monitor, provided with a screen 9, is linked to the generalization means 7 so that the user can see the results of the simulation just performed.

A printer, not represented, could also be provided and linked to the generalization means 7.

Represented in FIG. 2 is the possible evolution of the phases of a hair.

A given hair which is in the anagen phase A, that is to say the growth phase may, over a given elementary duration, remain in this same phase or evolve towards the telogen phase T or ceasing of growth phase.

The passage of the hairs from the anagen phase A to the telogen phase T is a phenomenon which is analysed statistically by considering that the hairs remain in the anagen phase A for a duration whose mean is equal to $\mu_A$ and whose standard deviation is equal to $\sigma_A$.

The hairs remain in the telogen phase T for a duration whose mean is $\mu_T$ and whose standard deviation is $\sigma_T$ and normally evolve towards the disappearance state D.

The hairs remain disappeared for a duration having mean $\mu_D$ and standard deviation $\sigma_D$ and thereafter evolve either towards a new anagen phase A, or towards a death phase Dd in which they remain permanently.

The head of hair is modelled by a discrete network which represents its surface. The number of points or nodes of this network corresponds to the number of hair follicles. Typically, for a simulation, the evolution of some 100 hair follicles will be taken into account.

The follicular automaton model characterizes each follicle by its spatial position within the network, its state (A, T, D, Dd), the remaining duration of its stay in the relevant phase as well as the number of cycles performed by this follicle.

The term cycle is understood to mean the passage of a follicle through the three states, anagen, telogen and disappeared, with return to the anagen phase.

The follicles are considered to evolve independently of their neighbours and the time is taken to be a discrete variable which can be counted in months, or even weeks.

The duration of the anagen, telogen and disappearance phases is characterized by distributions whose mean values $\mu_A, \mu_T, \mu_D$, and standard deviations $\mu_A, \mu_T, \mu_D$ are determined on the basis of experimental data which will have been stored in the system.

The mathematical form of distribution for the duration x of the various phases will be a distribution of negative-exponential type or preferably a log-normal distribution.

Figure 3:
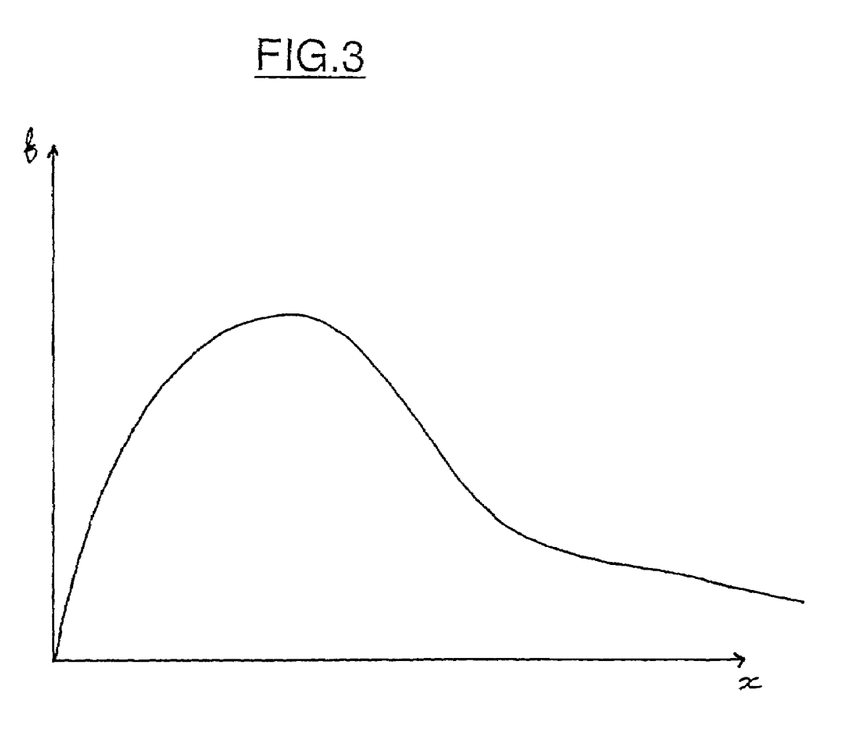
FIG. 3 is a log-normal type distribution curve.

The log-normal distribution function may be written:

$$f(x; \mu, \sigma) = \frac{1}{x\sqrt{2\pi\sigma}} \exp\left[-\frac{1}{2\sigma^2}(\log x - \mu)^2\right]$$

At the beginning of the simulation, the initial state of each follicle is fixed: start phase (A or T or D), number of follicular cycles $n_c$ already performed by each follicle, mean and standard deviation of each distribution, duration of the first phase corresponding to the chosen distribution.

The model is then made to evolve iteratively via time steps, equal for example to one month.

The modelled follicles are tested to determine those for which the moment has arrived to perform the next transition.

These follicles pass to the next state in the sequence of the cycle A→T→D→A.

The number of complete cycles performed by each follicle is counted.

If a follicle has reached a critical number of cycles $N_k$, it dies and passes to the state Dd where it remains permanently. $N_k$ is, in general, between 20 and 25.

The parameters of the model may possibly evolve over time.

The duration of the various phases A, T or D can decrease or increase according to hypotheses which may be added.

For each time step, the proportions of follicles in the various states A, T, D or Dd are calculated.

The number of follicular cycles performed by each of the follicles is calculated.

Then, we return to the first step of incrementing the discrete time variable until the final duration of the simulation is reached.

One thus succeeds in reproducing behaviours which are qualitatively and quantitatively in agreement with the experimental observations.

This modelling reproduces the distribution of the follicles in phases A, T and D.

By way of example, it is found that alopecic individuals are characterized, among other things, by shorter mean durations of the anagen phase than individuals not suffering from alopecia.

For alopecic individuals, this is manifested as a smaller fraction of hairs in the anagen phase than for the others.

It is interesting to make the mean duration of the anagen phase evolve over time by providing a law of decrease.

By virtue of the model, it is possible to simulate the long-term effect of an increase or of a reduction in the mean duration of the various phases.

It is then possible to track the appearance of alopecia or its disappearance according to the hypotheses considered, and thus simulate the effect of various internal or external factors.

The model also makes it possible to envisage the consequences of the death of the follicles after a critical number $N_k$ of follicular cycles for a given individual.

The hypothesis is created that each follicle can perform only a finite number of cycles.

As a result, the shorter the durations of the anagen phases, the more marked is the tendency for the hairs to be lost permanently.

The mean duration of the anagen phases will be a function which will depend on the spatial position of the hair on the scalp of the user, this function being implemented by the generalization means 7 of FIG. 1.

By way of example, a mean duration $\mu_A$ of the anagen phase can be assigned a duration of three months at the vertex, a region which is liable to be affected by alopecia, and of 20 months on the sides, a region which is appreciably less prone to alopecia.

Stated otherwise, the evolution of a hair is modelled by the following array.

| I | J | State | $n_c$ | Duration |
|---|---|---|---|---|
| 15 | 15 | A | 3 | 6 |
| 15 | 15 | A | 3 | 5 |
| 15 | 15 | A | 3 | 4 |
| 15 | 15 | A | 3 | 3 |
| 15 | 15 | A | 3 | 2 |
| 15 | 15 | A | 3 | 1 |
| 15 | 15 | A | 3 | 0 |
| 15 | 15 | T | 3 | 2 |
| 15 | 15 | T | 3 | 1 |
| 15 | 15 | T | 3 | 0 |
| 15 | 15 | D | 3 | 3 |
| 15 | 15 | D | 3 | 2 |
| 15 | 15 | D | 3 | 1 |
| 15 | 15 | D | 3 | 0 |
| 15 | 15 | A | 4 | 10 |

With I and J, the spatial coordinates of the follicle and $n_c$ the number of cycles which it has already performed.

On the basis of an observation carried out on the number of cycles $n_c$ at the instant of observation is estimated in accordance with the age of the user and the state of their head of hair, or possibly that of the scalp insofar as the latter may exhibit, with age and alopecia, a few disorders or anomalies of pigmentation and/or of relief which can be detected by the observation means.

The duration of each cycle which is assigned to each transition results from the drawing of a random number x performed using a random number generator provided in the simulation means and to which the log-normal function is applied in such a way as to determine the said duration assigned to a given phase.

The variable $n_c$ is incremented with each transition from the disappeared state D to the anagen phase A. When $n_c$ becomes equal to the critical number of cycles $N_k$, then the hair passes to the death phase Dd where it remains permanently.

For a user, two observations will therefore be performed separated by a specified duration, for example of the order of one month.

In the case, for example, of observations carried out with the videotrichogram technique, the procedure may be as follows:

an area of the scalp of the order of a cm² is completely shaved and then, a few days later, for example two or three, a snapshot of the said area which was shaved is captured by means of the camera 1.

It is thus possible, by virtue of the classification means, to determine which phase each hair is in.

Specifically, the hairs in the anagen phase will have grown appreciably, the hairs in the telogen phase will not have grown or will hardly have grown, the disappeared hairs and the dead hairs will be temporarily or permanently absent.

After the predetermined duration, for example of the order of 1 to 3 months, a second videotrichogram is performed according to the same procedure.

Thereafter, by comparing the two videotrichograms, a mean duration and a standard deviation of each phase are thereby determined, thus making it possible to operate the model.

In the follicular automaton model, there may also be provision to make the means $\mu_A$, $\mu_T$ and $\mu_D$ evolve, on the basis of the initial data gathered using the videotrichograms, as a function of the number of cycles already performed $n_c$, by providing for the progressive shortening of the mean durations.

To improve the quality of the generalization performed by the generalization means 7 of FIG. 1, it will be possible always to perform the observations at the same place on the scalp of all the users in such a way as to be able to apply the same generalization to all. Alternatively, the spatial coordinates of the hair region subjected to the observations will be indicated to the generalization means 7 so as to allow the effective and realistic simulation of the evolution of the entire head of hair, and to do so over several years, or even tens of years.

The user benefits from a forecast at various times, from 6 months to 100 years for example.

This forecast can also pertain to indirect parameters such as the coverage of the head of hair in addition to the phase parameters, and be coupled with a simulation of the evolution of the face, for example of the number of wrinkles, of the sagging of the eyelids and of any clinical sign associated with ageing.

The invention claimed is:

1. System for the simulation and predictive analysis of the evolution of a region of the scalp of a subject over time, comprising a means of observation of the said hair region able to output digital observation data, a first digital data processing means capable of classifying elementary parts of the said region on the basis of the observation data, a second digital data processing means capable of simulating the evolution of the said hair region as a function of the data emanating from the first digital data processing means, the second processing means comprising a means for applying to each observed hair a duration of continuation in its prevailing phase, on the basis of a distribution of phase durations and a random number, and a means of displaying the data emanating from the second digital data processing means, the data output by the first processing means comprising at least one classification according to the duration of the phases of the hair cycle.

2. System according to claim 1, wherein the observation data, output by the first processing means, comprise the surface density of hairs, the proportion A of hairs in the anagen phase, the proportion T of hairs in the telogen phase, the proportion D of disappeared hairs, the proportion Dd of hairs in the dead phase and the individual rate of growth of the hairs.

3. System according to claim 2, wherein the second processing means comprises a means for estimating the number of cycles $n_c$ performed by an observed hair, and for comparing it with a predetermined maximum number of cycles $N_k$, a cycle being defined by the successive passage through the three states, anagen, telogen and disappeared.

4. System according to any one of claims 2 to 3, wherein the second processing means comprises a matrix of probabilities of transition from one phase to another phase.

5. System according to any one of claims 2 to 3, wherein the second processing means comprises a means for allocating a given duration of phase to a hair.

6. System according to claim 5, wherein the means for allocating a given duration of phase to a hair comprises a random number generator and a means for comparing the said random number with aggregate probabilities of phase transition.

7. System according to any one of claims 2, wherein the second processing means comprises a matrix representative of the influence of data relating to neighbouring hairs on the transition from one phase to another phase.

8. System according to any one of claims 2, wherein the second processing means comprises a table representative of the evolution of the mean values of duration of the anagen, telogen and disappearance phases.

9. System according claim 1, comprising a means for performing a third processing for simulating the evolution of the entire head of hair of the subject on the basis of the data emanating from the second processing means.

10. System according to claim 9, comprising a means for associating data relating to the evolution of other sites with the data emanating from the third processing means.

11. Process for the simulation and predictive analysis of the evolution of a region of the scalp of a subject over time, in which:
the said hair region is observed so as to provide observation data,
a first digital processing of the observation data is performed so as to classify elementary parts of the said region,
a second digital processing is performed so as to perform a simulation of the temporal evolution of the said hair region as a function of the data emanating from the first digital processing means, the second digital processing comprising applying to each observed hair a duration of continuation in its prevailing phase, on the basis of a distibution of the phase durations and of random number, and
data emanating from the second digital processing are displayed, the data output by the first processing means comprising at least one classification according to the duration of the phases of the hair cycle.

12. Process according to claim 11, in which at least two observations are performed separated by a first given duration, each observation being preceded by a step of shaving the said hair region, the shaving step being separated from the corresponding observation by a second given duration, in such a way that an evolution of the said hair region can be noted, the observation data comprising the surface density of hairs, the proportion A of hairs in the anagen phase, the proportion T of hairs in the telogen phase, and the individual rate of growth of the hairs.

13. Process according to claim 12, in which, on the basis of the observation data, the hair coverage produced per unit time and area is calculated.

14. Process according to claim 11, in which the second digital processing takes into account the ratios of the durations of the anagen and telogen phases.

15. Process according to claim 11, in which a third digital processing is performed so as to perform a simulation of the temporal evolution of the entire head of hair of the subject on the basis of the data emanating from the second digital processing and the data emanating from the third digital processing are displayed by flat projection.

16. Process according to claim 15, in which, data from simulating the evolution of the face are associated with the data emanating from the third digital processing and the associated data are displayed.

17. System according to claim 16, comprising a means for performing a third processing for simulating the evolution of the entire head of hair of the subject on the basis of the data emanating from the second processing means.

18. System according to claim 17, comprising a means for associating data relating to the evolution of other sites with the data emanating from the third processing means.

19. System for the simulation and predictive analysis of the evolution of a region of the scalp of a subject over time, comprising a means of observation of the said hair region able to output digital observation data, a first digital data processing means capable of classifying elementary parts of the said region on the basis of the observation data, a second digital data processing means capable of simulating the evolution of the said hair region as a function of the data emanating from the first digital data processing means, the second processing means comprising a means for estimating the number of cycles $n_c$ performed by an observed hair, and for comparing it with a predetermined maximum number of cycles $N_k$, a cycle being defined by successive passage through the three states, anagen, telogen and disappeared, and a means of displaying the data emanating from the second digital data processing means, the data output by the first processing means comprising at least one classification according to the duration of the phases of the hair cycle.

20. System according to claim 19, wherein the observation data, output by the first processing means, comprise the surface density of hairs, the proportion A of hairs in the anagen phase, the proportion T of hairs in the telogen phase, the proportion D of disappeared hairs, the proportion Dd of hairs in the dead phase and the individual rate of growth of the hairs.

21. System according to claim 19 or 20, wherein the second processing means comprises a matrix of probabilities of transition from one phase to another phase.

22. System according to claim 19 or 20, characterized in that the second processing means comprises a means for allocating a given duration of phase to a hair.

23. System according to claim 21, wherein the means for allocating a given duration of phase to a hair comprises a random number generator and a means for comparing the said random number with aggregate probabilities of phase transition.

24. System according to claim 19, wherein the second processing means comprises a matrix representative of the influence of data relating to neighbouring hairs on the transition from one phase to another phase.

25. System according to claim 19, wherein the second processing means comprises a table representative of the evolution of the mean values of duration of the anagen, telogen and disappearance phases.

26. Process for the simulation and predictive analysis of the evolution of a region of the scalp of a subject over time, in which:
the said hair region is observed so as to provide observation data,
a first digital processing of the observation data is performed so as to classify elementary parts of the said region,
a second digital processing is performed so as to perform a simulation of the temporal evolution of the said hair region as a function of the data emanating from the first digital processing means, the second digital processing comprising estimating the number of cycles $n_c$ performed by an observed hair, and comparing it with a predetermined maximum number $N_k$, a cycle being defined by the successive passage through the three states, anagen, telogen and disappeared, and
data emanating from the second digital processing are displayed, the data output by the first processing means comprising at least one classification according to the duration of the phases of the hair cycle.

27. Process according to claim 26, in which at least two observations are performed separated by a first given duration, each observation being preceded by a step of shaving the said hair region, the shaving step being separated from the corresponding observation by a second given duration, in such a way that an evolution of the said hair region can be noted, the observation data comprising the surface density of hairs, the proportion A of hairs in the anagen phase, the proportion T of hairs in the telogen phase, and the individual rate of growth of the hairs.

28. Process according to claim 27, in which, on the basis of the observation data, the hair coverage produced per unit time and area is calculated.

29. Process according to claim 26, in which the second digital processing takes into account the ratios of the durations of the anagen and telogen phases.

30. Process according to claim 26, in which a third digital processing is performed so as to perform a simulation of the temporal evolution of the entire head of hair of the subject on the basis of the data emanating from the second digital processing and the data emanating from the third digital processing are displayed by flat projection.

31. Process according to claim 30, in which, data from simulating the evolution of the face are associated with the data emanating from the third digital processing and the associated data are displayed.

* * * * *